United States Patent
Pieper et al.

(10) Patent No.: US 7,060,894 B2
(45) Date of Patent: Jun. 13, 2006

(54) DEVICE FOR CONNECTING MICROCOMPONENTS

(75) Inventors: Guido Pieper, Darmstadt (DE);
Michael Schmelz, Griesheim (DE);
Hanns Wurziger, Darmstadt (DE);
Norbert Schwesinger, Eching (DE)

(73) Assignee: Merck Patent GmbH, Darmstadt (DE)

( * ) Notice: Subject to any disclaimer, the term of this patent is extended or adjusted under 35 U.S.C. 154(b) by 372 days.

(21) Appl. No.: 10/468,083

(22) PCT Filed: Jan. 23, 2002

(86) PCT No.: PCT/EP02/00610

§ 371 (c)(1),
(2), (4) Date: Aug. 15, 2003

(87) PCT Pub. No.: WO02/064247

PCT Pub. Date: Aug. 22, 2002

(65) Prior Publication Data

US 2004/0074084 A1    Apr. 22, 2004

(30) Foreign Application Priority Data

Feb. 15, 2001    (DE) ................. 101 06 996

(51) Int. Cl.
*H05K 5/06*    (2006.01)
(52) U.S. Cl. .............. 174/52.3; 361/788; 361/801; 422/103
(58) Field of Classification Search ........... 174/52.3; 422/103; 361/788, 789, 801, 802
See application file for complete search history.

(56) References Cited

U.S. PATENT DOCUMENTS

| 5,250,263 | A | | 10/1993 | Manz |
| 5,746,976 | A | * | 5/1998 | Yamada et al. ............... 422/62 |
| 5,964,239 | A | | 10/1999 | Loux et al. |
| 6,122,825 | A | | 9/2000 | Mayeaux |
| 6,240,790 | B1 | | 6/2001 | Swedberg et al. |
| 6,450,047 | B1 | | 9/2002 | Swedberg et al. |
| 6,929,781 | B1 | | 8/2005 | Hohmann et al. |

FOREIGN PATENT DOCUMENTS

| DE | 19854096 | | 5/2000 |
| DE | 19952764 | | 5/2000 |
| DE | 199 52 764 | * | 5/2002 |

OTHER PUBLICATIONS

International Search Report dated Apr. 15, 2002.
European Abstract of Japan Publication No. 58137807 dated Feb. 10, 1982.

* cited by examiner

*Primary Examiner*—Hung V. Ngo
(74) *Attorney, Agent, or Firm*—Millen, White, Zelano, Branigan, P.C.

(57) ABSTRACT

In a device for connecting microcomponents, in particular microreactors, which preferably have a plate-shaped design and preferably consist of silicon, a sealing plate having apertures which correspond to apertures in the microcomponents is arranged between the microcomponents.

11 Claims, 1 Drawing Sheet

DEVICE FOR CONNECTING MICROCOMPONENTS

Figure 1:
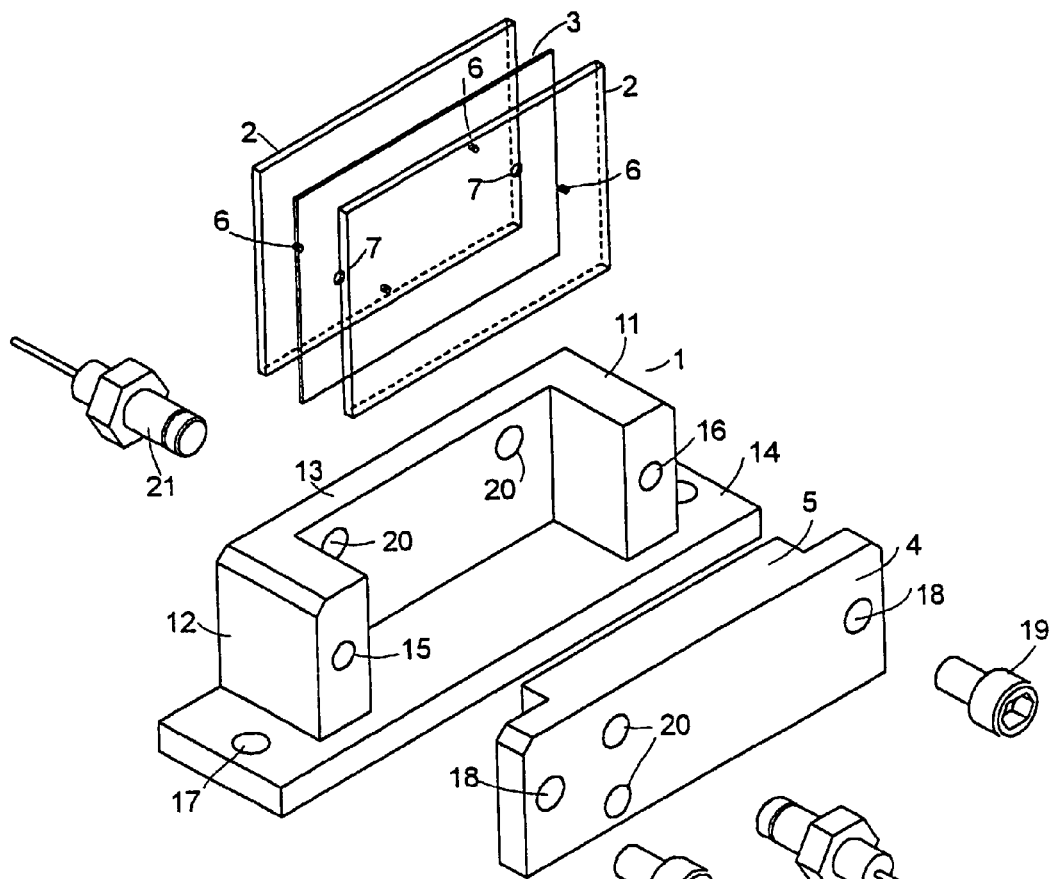

The invention relates to a device for connecting microcomponents, in particular microreactors, which preferably have a plate-shaped design and preferably consist of silicon.

The development and preparation of novel substances in the area of chemistry frequently necessitates extensive series of experiments. For this purpose, microcomponents have been disclosed with the aid of which the experiments can be carried out with small amounts. The modular construction of these microcomponents, for example microreactors and other components for the treatment of various substances, facilitates easy assembly of systems for the particular task. A modular chemical microsystem of this type is described in DE 199 17 398 A1. In this microsystem, the various microcomponents are connected to a control bus via control connections and to a substance channel system via substance connections. However, the making of the multiplicity of substance connections is quite complicated. In particular, it is even necessary here to transfer substances from one microcomponent to an adjacent one via the substance channel system. Furthermore, a connection support for plate-shaped microcomponents is disclosed in DE 198 54 096 A1.

The object of the present invention is to facilitate simple transfer of the substances from one microcomponent to another.

This object is achieved in accordance with the invention in that a sealing plate having apertures which correspond to apertures in the microcomponents is arranged between the microcomponents. It is preferably provided that the sealing plate consists of an elastic material which is resistant to the respective media treated in the microcomponents. For a large number of substances to be treated, it is advantageous for the material to be polytetrafluoroethylene.

The device according to the invention has the advantage that connections for the transport of liquid substances and possibly also gaseous substances are possible between adjacent microcomponents in an extremely simple and reliable manner. No special connection device is necessary on the part of the microcomponents, which preferably consist of a fracture-sensitive silicon crystal. Simple holes are sufficient. In addition, the requisite leak tightness is attained in the device according to the invention.

The individual microcomponents may be, for example, reactors, pumps, mixers, residence zones, extractors or heat exchangers, which can be assembled to form a complex microsystem in the manner of a construction kit. To this end, apart from a functionally correct arrangement of the respective aperture, alternating layering of the microcomponents and the sealing plates is necessary.

Should polytetrafluoroethylene not be suitable for the respective substances, other materials having corresponding chemical resistance and having the requisite mechanical properties, in particular elasticity and surface quality, are also available, for example perfluoroelastomers or polyvinylidene fluoride.

A good sealing action arises in the device according to the invention if it is provided, in accordance with an advantageous embodiment, that the sealing plate essentially has the size of the adjacent surface of the microcomponents. However, should the microcomponents only have a planar surface in part, and additional components project on other parts of the surface, the device according to the invention may also be refined in such a way that the sealing plate covers a region of the adjacent microcomponents which is provided with apertures and leaves a further region of the adjacent microcomponents uncovered.

The arrangement of the sealing plates between the microcomponents can be achieved in various ways. In the case of use of the entire arrangement as disposable apparatus, permanent joining techniques, such as adhesive bonding, riveting and encapsulation in or with synthetic resin, are possible. However, a detachable and nevertheless leak-tight connection between the microcomponents can be achieved by pressing the microcomponents against one another. To this end, various techniques are likewise available, for example sprung snap-fit connections—similar to a chest lock—sprung or screwable clips, bolt/bayonet locks or electromagnetically, pneumatically or hydraulically driven clamping devices.

Due to the modular construction, replacement or repair of individual microcomponents is possible without the entire modular system having to be replaced in the event of a fault.

In another refinement of the device according to the invention, it is proposed that a holder for pressing the microcomponents against one another has a U-shaped accommodation part for the microcomponents with two arms whose ends can be screwed to a pressure plate. The force necessary for sealing is thus distributed uniformly over the surface of the microcomponents, protecting the fracture-sensitive silicon microcomponents against destruction.

In order to be able to clamp microcomponent and sealing plate stacks of different thickness using a single holder, it is proposed, in accordance with an advantageous embodiment, that the pressure plate has a thickened central part, which fits between the arms of the U-shaped accommodation part.

Another advantageous embodiment enables connections to the outside through threaded holes for the accommodation of connection elements being provided in the pressure plate and in the region of the U-shaped accommodation part which is opposite the pressure plate.

Figure 2:
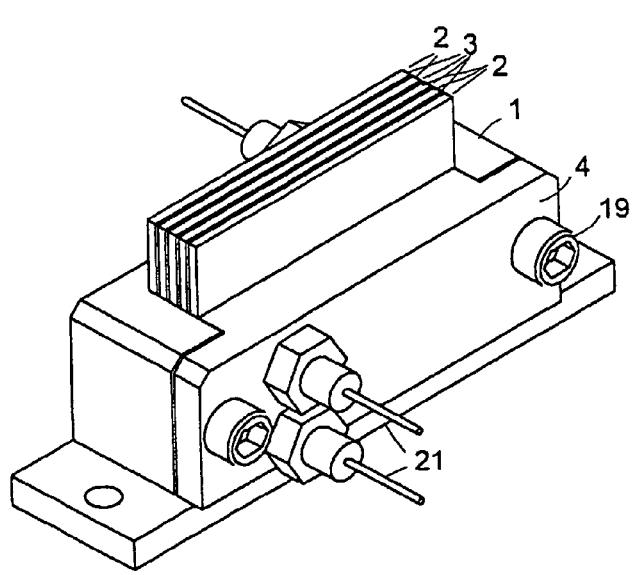

Illustrative embodiments of the invention are explained in greater detail below and are shown in the drawing with reference to a number of figures, in which:

FIG. 1 shows an exploded view of the parts of a device according to the invention, and FIG. 2 shows the parts of a device according to the invention in the assembled state, with a greater number of microcomponents being provided in FIG. 2 compared with the depiction in FIG. 3.

In FIG. 1, provision is made for two microcomponents 2 having apertures 6, through which substances are transported from one microcomponent to the other. To this end, a sealing plate 3 having two apertures 7, which correspond to the apertures 6, is arranged between the two microcomponents 2. The microcomponents 2 are pressed against one another in a holder.

The holder consists of a U-shaped accommodation part 1 having two arms 11, 12 and a base part 13 which connects the arms 11, 12. The U-shaped accommodation part 1 is arranged on an assembly plate 14, which can in turn be attached in a larger overall system with the aid of holes 17. Threaded holes 15, 16 are provided on the front faces of the arms 11, 12, enabling a pressure plate 4, which is provided with through-holes 18, to be attached with the aid of screws 19.

The pressure plate 4 is thickened in the central region 5, so that it penetrates between the arms 11, 12, and stacks of different thickness can thus be pressed reliably against one another with simultaneous guidance through the arms 11, 12.

In the base part 13 and in the pressure plate 4, threaded holes 20 are provided, into which can be screwed connection elements 21, which serve as connections for the supply and discharge of substances from and to outside the system described. The connection elements are each provided with sealing discs 22 on their front face.

FIG. 2 shows a device according to the invention in the assembled state, with five microcomponents 2 being connected to one another, in each case with interposition of sealing plates 3.

The invention claimed is:

1. A device for connecting at least two microcomponents (2) which comprises:
    arranged between the microcomponents (2), a sealing plate (3) having apertures (7) which correspond to apertures (6) in the microcomponents (2),
    a holder (1) with a U-shaped accommodation part and two arms (11, 12) for accommodating the microcomponents (2) and sealing plate and
    a pressure plate (4) screwable to the holder (1) which presses the microcomponents together against the sealing plate when screwed to the holder (1).

2. The device of claim 1, wherein the at least two microcomponents are microreactors.

3. The device of claim 2, wherein the microreactors have a plate-shaped design.

4. The device of claim 2, wherein the microreactors are made of silicon.

5. The device of claim 3, wherein the microreactors are made of silicon.

6. The device of claim 1, wherein the sealing plate (3) consists of an elastic material which is resistant to the respective media to be treated in the microcomponents (2).

7. The device of claim 6, wherein the elastic material is polytetrafluoroethylene.

8. The device according to claim 1, wherein the adjacent surfaces of the sealing plate (3) and the at least two microcomponents (2) have essentially the same surface area and contact one another over essentially the entire surface area of the adjacent surfaces.

9. The device according to claim 1, wherein the sealing plate is of a surface area covering a region of the adjacent contacting surface areas of the at least two microcomponents which is provided with apertures but not covering at least one other region of the adjacent surface area at least one of the adjacent microcomponents.

10. The device according to claim 1, wherein the pressure plate (4) has a thickened central part (5) which fits between the arms (11, 12) of the U-shaped accommodation part of the holder (1) when screwed into the holder (1).

11. The device according to claim 1, wherein the pressure plate (4) has at least one threaded hole (20) corresponding to an aperture (6) of the microcomponent which comes into contact with the pressure plate (4) when screwed into the holder (1) andlor the U-shaped accommodation part of the holder (1) has at least one threaded hole (20) corresponding to an aperture (6) of the microcomponent which comes into contact with the accommodation part of the holder when the pressure plate (4) is screwed into the holder (1), such that a connection element (21) can be provided to the threaded hole(s) in communication with the corresponding aperture(s) (6).

* * * * *